United States Patent
Meyer et al.

(10) Patent No.: US 7,141,681 B2
(45) Date of Patent: Nov. 28, 2006

(54) CONTINUOUS PROCESS FOR PREPARING DIHYDROPYRONES

(75) Inventors: Oliver Meyer, Dorsheim (DE); Markus Sauter, Gensingen (DE); Mark Goehlich, Appenheim (DE)

(73) Assignee: Boehringer Ingelheim Pharma GmbH & Co. KG (DE)

( * ) Notice: Subject to any disclaimer, the term of this patent is extended or adjusted under 35 U.S.C. 154(b) by 805 days.

(21) Appl. No.: 10/075,956

(22) Filed: Feb. 14, 2002

(65) Prior Publication Data

US 2002/0161037 A1 Oct. 31, 2002

Related U.S. Application Data

(60) Provisional application No. 60/272,118, filed on Feb. 28, 2001.

(30) Foreign Application Priority Data

Feb. 22, 2001 (DE) ............... 101 08 471

(51) Int. Cl.
*C07D 309/30* (2006.01)
(52) U.S. Cl. .................................... 549/292
(58) Field of Classification Search ............... 549/313, 549/417, 292
See application file for complete search history.

(56) References Cited

FOREIGN PATENT DOCUMENTS

| WO | WO 95 14012 | 5/1995 |
|----|----|----|
| WO | WO 98/19997 A2 | 5/1998 |
| WO | WO 98/19997 A3 | 5/1998 |
| WO | WO 98 37457 | 8/1998 |
| WO | WO 00 15625 | 3/2000 |
| WO | WO 01 09064 | 2/2001 |
| WO | WO 01 51434 | 7/2001 |

OTHER PUBLICATIONS

Erfeld, W et al 'Characterization of mixing in micromixers by a test reaction: single mixing unites and mixer arrays' Ind. Eng. Chem. Res. 1999, 38(3), 1075-1082.*
Hawley's Condensed Chemical Dictionary, 13th Ed. (1997) p. 1004.*
Steve R. Turner, Tipranavir (PNU-140690): A Potent, Orally Bioavailable Nonpeptidic HIV Protease Inhibitor of the 5, 6,-Dihydro-4-hydroxy-2-pyrone Sulfonamide Class, J. Med. Chem. 1998, vol. 41 3467-3476.
Autorenkollerktiv; Organikum 1976 VEB Deutscher Verlag der Wissenschaften, Berlin; pp. 579-589—XP002200333.
Kamper, K.P., et al; Micro electro mechanical systems; 1997; MEMS' 97; Proceedings, IEEE, Tenth Annual Int'l. Workshop on Nagoya, Japan, Jan. 26-30, 1997 NY, NY USA, IEEE, US; pp. 338-343.
"Microreactiors find new niches"; Chemical Engineering, McGraw-Hill; New York, U.S. pp. 30-31, 33.
Ehrfeld W. et al, Dechema Monographien, Verlag Chemie, Weinheim, DE, vol. 132, 1995 pp. 1-28.
Tait, Bradley, D., et al., 4-Hydroxy-5-6-dihydrolpyrones. 2. Potent Non-Peptide Inhibitors of HIV Protease, J. Med. Chem. 1997, 40, 3781-3792.

* cited by examiner

*Primary Examiner*—Amelia A. Owens
(74) *Attorney, Agent, or Firm*—Michael P. Morris; Mary-Ellen Devlin; Anthony P. Bottino

(57) ABSTRACT

The invention relates to a continuous process for preparing dihydropyrones of general formula I,

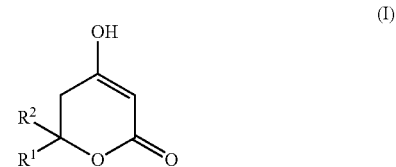

(I)

wherein the groups $R^1$ and $R^2$ have the meanings described herein.

11 Claims, No Drawings

CONTINUOUS PROCESS FOR PREPARING DIHYDROPYRONES

RELATED APPLICATIONS DATA

This application claims benefit to German application 10108471.4-44 filed Feb. 22, 2001 and U.S. provisional application Ser. No. 60/272,118 filed Feb. 28, 2001.

TECHNICAL FIELD OF THE INVENTION

The invention relates to an improved process for preparing dihydropyrones of general formula I,

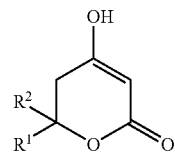

(I)

wherein the groups $R^1$ and $R^2$ may have the meanings given in the detailed description hereinbelow.

BACKGROUND TO THE INVENTION

Dihydropyrones are important as intermediate products in drug synthesis. In particular, 5,6-dihydro-4-hydroxy-6-phenethyl-6-propyl-2H-pyran-2-one is an important intermediate product in the synthesis of tipranavir, an HIV protease inhibitor. The compounds of formula I and processes for preparing them are known from the prior art, e.g. from International Patent Application WO 98/19997 and from the "Journal of Medicinal Chemistry, 1998, Vol. 41, No. 18". Recently, a process for preparing a racemic mixture of 5,6-dihydro-4-hydroxy-6-phenethyl-6-propyl-2H-pyran-2-one has been described, which comprises in step a) reacting a dianion of methylacetoacetate with 1-phenyl-3-hexanone and in a subsequent step b) cyclising the resulting β-ketoester by alkaline hydrolysis followed by acidification. This process is carried out discontinuously and achieves a 72% yield.

The problem of the invention is therefore to provide a process which enables dihydropyranones to be prepared with a high degree of purity and in a significantly improved yield compared with the prior art.

SUMMARY OF THE INVENTION

It is therefore an object of the invention to provide an improved process for preparing dihydropyrones of general formula I,

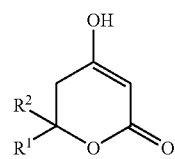

(I)

wherein the groups $R^1$ and $R^2$ may have the meanings given in the detailed description hereinbelow.

DETAILED DESCRIPTION OF THE INVENTION

Surprisingly, it has been found that the compounds of formula I can be obtained with a high degree of purity and in a significantly improved yield if step a) is carried out continuously in a microreactor.

The invention therefore relates to a process, suitable for use in the laboratory and on an industrial scale, for preparing a compound of general formula (I),

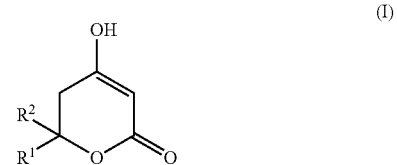

(I)

wherein
$R^1$ denotes a $C_1$–$C_8$-alkyl, $C_6$–$C_{10}$-aryl-$C_1$–$C_4$-alkyl or $C_3$–$C_8$-cycloalkyl-$C_1$–$C_4$-alkyl group, and
$R^2$ denotes a $C_1$–$C_8$-alkyl group,
a) by reacting a ketone of formula (II)

(II)

wherein $R^1$ and $R^2$ are as hereinbefore defined,
with an acetoacetate in the presence of a strong base and
b) by cyclising the resulting compound of formula (IV)

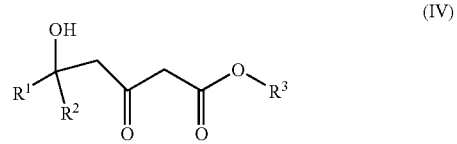

(IV)

wherein
$R^3$ denotes a $C_1$–$C_4$-alkyl or benzyl group,
wherein the ketone of formula II is continuously reacted with an acetoacetate in the form of its dianion in a microreactor.

The microreactors which are suitable for the process according to the invention are known, for example, from "Microreactors; Wolfgang Ehrfeld, Volker Hessel, Holger Löwe; Wiley-VCH;ISBN 3-527-29590-9; Chapter 3 Micromixers". Microreactors which may be used in the process according to the invention generally have a housing made of stainless steel, glass, titanium or metal alloys and an inlay or inlay structures of thermally oxidised silicon, copper, aluminium, nickel, silver, metal alloys, Foturan glass or metal-coated plastics, glass or ceramic materials.

The educt currents may be mixed both turbulently as well as by laminar flow, preferably by laminar flow. The preferred channel structures for laminar mixing generally include interdigital structures, star-shaped structures or structures of a worm-type mixer. Types of microreactor which may be used for the process according to the invention may be obtained, for example, from the companies Institut für Mikrotechnik Mainz GmbH, Cellular Process Chemistry GmbH or Mikroglas AG.

Particularly preferred according to the invention is a process wherein a microreactor with an interdigital channel structure, most preferably a microreactor of the LIGA type (produced by Lithographie, Galvanoformung, Abformung [lithography, electroforming and moulding]) with an interdigital channel structure, produced for example by the Institut für Mikrotechnik Mainz GmbH, is used for reaction step a).

Particularly preferred is a process wherein a current of educt A containing the compound of formula (II) and a current of educt B containing an acetoacetate in the form of a dianion are continuously mixed together in the mixing element of a microreactor and the liquid reaction mixture is conveyed into a capillary, particularly a holding capillary.

Also particularly preferred is a process wherein the capillary is 0.1 to 10 m, preferably 0.3 to 8 m, preferably 0.5 to 6 m, most preferably 0.8 to 4 m, particularly preferably about 1 m long and has an internal diameter of 0.05 to 5 mm, preferably 0.1 to 4 mm, preferably 0.3 to 3 mm, particularly preferably about 1 mm.

Particularly preferred is a process wherein 1-phenyl-3-hexanone is used as the compound of formula (II) in step a).

Also particularly preferred is a process wherein in step a) the acetoacetate is used in the form of a dilithium, monolithium, monosodium or disodium salt.

Of particular importance is a process wherein the molar ratio of the compound of formula (III) to the compound of formula (II) used is 2:1 to 1:2, preferably 1:1 to 1:1.5, particularly preferably 1:1 to 1:1.2, most preferably about 1:1.

Also of particular importance is a process wherein the reaction in step a) is carried out at a temperature of −78 to +85° C., preferably at −40 to +50° C., preferably at −30 to +20° C., more preferably at −25 to +10°C., particularly preferably at −20 to 0° C., most preferably at −15 to −5° C., especially preferably at about −10° C.

Also preferred is a process wherein the reaction in step a) is carried out at an overall flow rate, calculated by adding together the flow rates of the compound of formula II and the acetoacetate, of 1.5 to 5 ml/min, preferably at 1.8 to 4 ml/min, particularly preferably at 2 to 3.5 ml/min, particularly preferably at about 2.5 ml/min.

Also particularly preferred is a process wherein the flow rate of the compound of formula (II) to that of the acetoacetate is in a ratio of 1:1 to 1:2, preferably 1:1.1 to 1:1.8, particularly preferably 1:1.2 to 1:1.5, particularly preferably about 1:1.3.

To achieve these flow rates it is generally advantageous to use low-vibration pumps, preferably rotary pumps, preferably ceramic rotary pumps or HPLC pumps. The flow rates may be adapted to different types of reactors to obtain the optimum space/time yield.

Also particularly preferred is a process wherein the reaction is carried out in a plurality of microreactors connected in series or in parallel.

The 5,6-dihydro-4-hydroxy-6-phenethyl-6-propyl-2H-pyran-2-one obtained according to the invention is preferably used to prepare tipranavir.

In the present invention, the term "alkyl" denotes a straight-chain or branched alkyl group with 1 to 8 carbon atoms, preferably 2 to 7 carbon atoms, preferably 3 to 6 carbon atoms. Methyl, ethyl, n-propyl, isopropyl, n-butyl, isobutyl, sec. butyl, tert.butyl, n-pentyl, isopentyl or neopentyl are particularly preferred.

The term "aryl" denotes an aromatic hydrocarbon group with 6 to 10 carbon atoms, preferably phenyl or naphthyl, particularly preferably phenyl, which may be substituted by one or more alkyl groups.

Examples of cycloalkyl groups with 3–8 carbon atoms include cyclopropyl, cyclobutyl, cyclopentyl, cyclohexyl, cycloheptyl or cyclooctyl.

$R^1$ is preferably phenylmethyl, phenylethyl or phenylpropyl, most preferably 2-phenylethyl, $R^2$ is preferably methyl, ethyl, n-propyl or n-butyl, most preferably n-propyl. $R^3$ is preferably methyl, ethyl, n-propyl or benzyl, most preferably ethyl.

Metal hydrides, metal organyls, metal amides, metal dialkylamides or metal hexamethyldisilazanes are preferably used as strong bases.

Examples of metal cations include lithium, sodium, potassium, rubidium, caesium, magnesium, calcium, titanium, silicon, tin and lanthanoids, preferably lithium or sodium, most preferably lithium.

Particularly preferred bases are sodium hydride, lithium diethylamide, butyl lithium, lithium diisopropylamide, lithium hexamethyl disilazane, sodium hexamethyl disilazane or potassium hexamethyl disilazane or combinations thereof. As a rule, 2 or more equivalents of these bases are used, preferably 1.8 to 3.0, particularly 1.9 to 2.5 equivalents. The acetoacetate is generally in the form of a dianion of formula III in the presence of these bases.

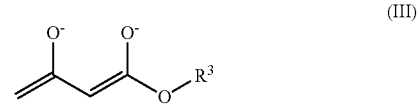

The process according to the invention is generally carried out in the presence of an inert diluent. Preferred diluents are non-polar organic solvents such as e.g. aliphatic or aromatic hydrocarbons, ethers or mixtures thereof. In a particularly preferred embodiment, the diluent is selected from among dimethoxyethane, diethylether, tert-butyl-methylether, tetrahydrofuran, n-hexane, cyclohexane, toluene, xylene or a mixture of these solvents, particularly tetrahydrofuran and dimethoxyethane.

In addition to the abovementioned diluents the reaction may also contain one or more amines such as, for example, diethylamine, diisopropylamine or tetramethylethylenediamine.

The advantage of the process according to the invention is in the high purity and unexpectedly high yield of dihydropyranone of more than 90%, which results from the continuous microreactor process of step a). The compound of formula IV may be further processed as a product of the microreactor process without further purification.

The following examples serve to illustrate the process according to the invention still further. They are intended solely as examples of procedures without restricting the invention to their content.

EXAMPLE 1

5.6-dihydro-4-hydroxy-6-phenethyl-6-propyl-2H-pyran-2-one

Step a)

A mixture I of 81.9 g of 1-phenyl-3-hexanone and 840 ml of tetrahydrofuran and a mixture II of 72.9 g of ethyl-acetoacetate, 117 ml of diethylamine and 450 ml of n-butyllithium in n-hexane (2.5 molar) in 361 ml of tetrahydrofuran at −10° C. are pumped towards each other into a microreactor made by the company Institut für Mikrotechnik Mainz GmbH (of the Liga type with interdigital channel structure) and mixed together. The volume flow of mixture I is set to 1 ml/min and the volume flow of mixture II is set to 1.1 ml/min. The solution of product is passed through a capillary (length 1 m, diameter 1 mm) and then taken up in saturated ammonium chloride solution/hydrochloric acid solution at a pH of 5–6.

Step b)

140 g of the crude β-ketoester resulting from step a) are taken up in 200 ml of methanol at 5 to 10° C. Solid potassium hydroxide is added at 5 to 10° C. with stirring and then the mixture is stirred for about 15 hours at ambient temperature. The methanol is distilled off and the residue is mixed with 500 ml of water. It is extracted twice with 200 ml of toluene. After the organic phase has been separated off, another 400 ml of fresh toluene are added to the aqueous phase. This is acidified with conc. sulphuric acid to pH 1.9. The aqueous phase is separated off and the organic phase is extracted 3 times more with water. The organic phase is evaporated to dryness in vacuo (60 mbar) at 40° C. The crude product is dissolved in 200 ml of toluene at 60° C. and then filtered. 200 ml of n-octane are slowly added dropwise to the filtrate with stirring at 40° C. It is seeded with 5,6-dihydro-4-hydroxy-6-phenethyl-6-propyl-2H-pyran-2-one crystals and stirred for about 15 hours at ambient temperature. 400 ml of n-octane are added dropwise to the resulting crystal mass which is then cooled to 0–5° C. After stirring for about 1 hour at 0–5° C. the crystals are suction filtered, washed with n-octane and dried. The yield is 92%.

Analogously to Example 1, 5,6-dihydro-4-hydroxy-6-phenethyl-6-propyl-2H-pyran-2-one was prepared by carrying out step a) in a microreactor under the conditions specified in the following Table:

| Example No. | Temperature [° C.] | Volume flow I (1-phenyl-3-hexanone) [ml/min] | Volume flow II (Acetoacetate) [ml/min] | Yield of ketoester [HPLC % area] |
|---|---|---|---|---|
| 2 | −25 | 1 | 1 | 84.5 |
| 3 | −25 | 1 | 1.1 | 87.9 |
| 4 | −25 | 1 | 1.2 | 83.8 |
| 5 | −25 | 1 | 1.3 | 86.4 |
| 6 | −25 | 2 | 2.4 | 81.1 |
| 7 | −20 | 1 | 1.2 | 87.2 |
| 8 | −20 | 2 | 2.4 | 83.8 |
| 9 | −10 | 1 | 1.2 | 86.5 |
| 10 | −10 | 2 | 2.4 | 86.8 |
| 11 | 10 | 2 | 2.4 | 82.1 |

The invention claimed is:

1. A process for preparing a compound of general formula (I),

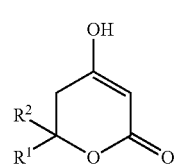

wherein
R$^1$ is a C$_1$–C$_8$-alkyl, C$_6$–C$_{10}$-aryl-C$_1$–C$_4$-alkyl or C$_3$–C$_8$-cycloalkyl-C$_1$–C$_4$-alkyl group, and
R$^2$ is a C$_1$–C$_8$-alkyl group, comprising:
reacting a) a ketone of formula (II)

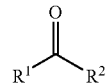

wherein R$^1$ and R$^2$ are as hereinbefore defined,
with an acetoacetate in the presence of a strong base and
b) cyclising the resulting compound of formula (IV)

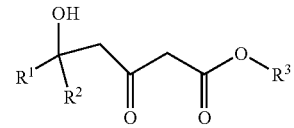

wherein
R$^3$ denotes a C$_1$–C$_4$-alkyl or benzyl group, by means of a base, wherein a compound of formula II is continuously mixed and reacted with an acetoacetate in the form of its dianion in a microreactor, and subsequently isolating the product compound of the general formula (I).

2. The process according to claim 1, wherein a microreactor with an interdigital channel structure is used for reaction step a).

3. The process according to claim 2, wherein a current of educt A containing the compound of formula (II) and a current of educt B containing the acetoacetate in the form of its dianion are continuously mixed together in the mixing element of a microreactor and the liquid reaction mixture is passed into a holding capillary.

4. The process according to claim 3, wherein the capillary is 0.1 to 10 m long and 0.05 to 5 mm in diameter.

5. The process according to claim 4 wherein 1-phenyl-3-hexanone is used as the compound of formula (II) in step a).

6. The process according to claim 5, wherein step a) the acetoacetate is used in the presence of at least 2 equivalents of a strong base selected from sodium hydride, butyllithium and lithium dialkylamide.

7. The process according to claim 6, wherein the acetoacetate is added to the compound of formula (II) in a molar ratio of 2:1 to 1:2.

8. The process according to claim 7 wherein the reaction in step a) is carried out at a temperature of −78 to +85° C.

9. The process according to claim 8, wherein the reaction in step a) is carried out at an overall flow rate of 1.5 to 5 ml/min.

10. The process according to claim 9, wherein the flow rate of the compound of formula (II) to the compound of formula (III) is in a ratio of 1:1 to 1:2.

11. The process according to claim 10 wherein the reaction is carried out in a plurality of microreactors connected in series or in parallel.

* * * * *